(12) United States Patent
Choi et al.

(10) Patent No.: US 11,911,189 B2
(45) Date of Patent: Feb. 27, 2024

(54) BIOSIGNAL PROCESSING METHOD AND APPARATUS

(71) Applicant: SAMSUNG ELECTRONICS CO., LTD., Suwon-si (KR)

(72) Inventors: Changmok Choi, Yongin-si (KR); Seungkeun Yoon, Seoul (KR); Ui Kun Kwon, Hwaseong-si (KR); Sang-Joon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1281 days.

(21) Appl. No.: 16/419,297

(22) Filed: May 22, 2019

(65) Prior Publication Data

US 2019/0269373 A1    Sep. 5, 2019

Related U.S. Application Data

(62) Division of application No. 15/271,255, filed on Sep. 21, 2016, now Pat. No. 10,335,093.

(30) Foreign Application Priority Data

Feb. 15, 2016   (KR) .................. 10-2016-0016901

(51) Int. Cl.
*A61B 5/02*    (2006.01)
*A61B 5/00*    (2006.01)
(Continued)

(52) U.S. Cl.
CPC ........ *A61B 5/7282* (2013.01); *A61B 5/02108* (2013.01); *A61B 5/02416* (2013.01);
(Continued)

(58) Field of Classification Search
CPC ............ A61B 5/02108; A61B 5/02416; A61B 5/02438; A61B 5/0452; A61B 5/681; A61B 5/7225; A61B 5/7235; A61B 5/7282

See application file for complete search history.

(56) References Cited

U.S. PATENT DOCUMENTS

| | | | |
|---|---|---|---|
| 5,243,992 | A | 9/1993 | Eckerle et al. |
| 8,870,782 | B2 | 10/2014 | Futatsuyama et al. |

(Continued)

FOREIGN PATENT DOCUMENTS

| | | |
|---|---|---|
| CN | 103800001 A | 5/2014 |
| CN | 103815892 A | 5/2014 |

(Continued)

OTHER PUBLICATIONS

Shin, Hang Sik, et al. "Adaptive threshold method for the peak detection of photoplethysmographic waveform." *Computers in Biology and Medicine*, vol. 39, Issue 12, Dec. 2009, (pp. 1145-1152).

(Continued)

*Primary Examiner* — Amanda K Hulbert
(74) *Attorney, Agent, or Firm* — NSIP Law

(57) ABSTRACT

A method and apparatus for processing a biosignal is disclosed. The apparatus may extract reference points from a waveform of a biosignal, determine a pulse direction of the biosignal based on the extracted reference points, and determine a feature point of the biosignal based on a feature point determining method corresponding to the determined pulse direction of the biosignal.

16 Claims, 14 Drawing Sheets

(51) Int. Cl.
*A61B 5/021* (2006.01)
*A61B 5/024* (2006.01)
*A61B 5/349* (2021.01)

(52) U.S. Cl.
CPC ........ *A61B 5/7235* (2013.01); *A61B 5/02438* (2013.01); *A61B 5/349* (2021.01); *A61B 5/681* (2013.01); *A61B 5/7225* (2013.01)

(56) References Cited

U.S. PATENT DOCUMENTS

| | | |
|---|---|---|
| 8,954,140 B2 | 2/2015 | Mottaiyan et al. |
| 9,119,546 B2 | 9/2015 | Lee et al. |
| 2006/0224074 A1 | 10/2006 | Ouchi et al. |
| 2012/0259182 A1 | 10/2012 | Kim et al. |
| 2013/0237868 A1 | 9/2013 | Choi et al. |
| 2013/0267859 A1 | 10/2013 | Okuda et al. |
| 2014/0249438 A1 | 9/2014 | Morikawa et al. |
| 2015/0359447 A1 | 12/2015 | Kanishima et al. |
| 2016/0022152 A1* | 1/2016 | Meriheinä ............ A61B 5/4812 600/485 |

FOREIGN PATENT DOCUMENTS

| | | |
|---|---|---|
| EP | 2 881 035 A1 | 6/2015 |
| JP | 62-57538 A | 3/1987 |
| JP | 5-184548 A | 7/1993 |
| JP | 2005-80712 A | 3/2005 |
| JP | 2006-280809 A | 10/2006 |
| JP | 2008-61824 A | 3/2008 |
| JP | 2012-139433 A | 7/2012 |
| JP | 5605253 B2 | 10/2014 |
| KR | 10-1308609 B1 | 9/2013 |
| KR | 10-1409800 B1 | 6/2014 |
| KR | 10-2015-0012462 A | 2/2015 |

OTHER PUBLICATIONS

Extended European search report dated Jun. 29, 2017 in corresponding European Patent Application No. 16205005.8 (9 pages in English).

Japanese Office Action dated Jul. 7, 2020 in counterpart Japanese Patent Application No. 2017-010317 (4 pages in English and 6 pages in Japanese).

Chinese Office Action dated Jul. 29, 2020 in counterpart Chinese Patent Application No. 201611019661.4 (15 pages in English and 10 pages in Chinese).

* cited by examiner

BIOSIGNAL PROCESSING METHOD AND APPARATUS

CROSS-REFERENCE TO RELATED APPLICATION(S)

This application is a divisional of U.S. patent application Ser. No. 15/271,255 filed on Sep. 21, 2016 which claims the benefit under 35 USC § 119(a) of Korean Patent Application No. 10-2016-0016901 filed on Feb. 15, 2016, in the Korean Intellectual Property Office, the entire disclosure of which is incorporated herein by reference for all purposes.

BACKGROUND

1. Field

The following description relates to a method and apparatus for processing a biosignal.

2. Description of Related Art

Research is being conducted on the application of information technology (IT) to medical technology. For example, research is being conducted on mobile healthcare relating to real-time monitoring of a health condition of a user during the daily life of the user, for example, at home and at work. Mobile healthcare may enable measurement of a biosignal of a user without restrictions of time and space, and estimation of a health condition of the user through an analysis of the measured biosignal. For example, in the mobile healthcare, an arrhythmia occurrence time or an arrhythmia type may be estimated by measuring and analyzing, in real time, an electrocardiogram (ECG) signal of a user suffering from a heart-related disease, and information about a result of the estimation may be provided to the user or concerned medical professionals and entities.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a biosignal processing method includes extracting reference points from a waveform of a biosignal, determining a pulse direction of the biosignal based on the extracted reference points, and determining a feature point of the biosignal based on a feature point determining method corresponding to the pulse direction.

A biosignal processing method including extracting reference points from a waveform of a biosignal, determining a pulse direction of the biosignal based on the extracted reference points, and determining a feature point of the biosignal based on a feature point determining method corresponding to the pulse direction.

The extracting of the reference points may include extracting candidate reference points corresponding to at least one of a maximum point or a minimum point from the waveform of the biosignal, and determining the reference points from among the candidate reference points based on signal values of the candidate reference points.

The determining of the reference points may include determining a first candidate reference point having a highest signal value to be a first reference point from among neighboring first candidate reference points, and determining a second candidate reference point having a lowest signal value to be a second reference point from among neighboring second candidate reference points.

The extracting of the candidate reference points may include determining the candidate reference points based on a highest signal value or a lowest signal value in a time interval of the waveform of the biosignal.

The determining of the pulse direction may include determining a pulse sharpness level corresponding to each of first reference points and second reference points, and determining the pulse direction based on the pulse sharpness level.

The determining of the pulse sharpness level may include determining a pulse sharpness level corresponding to the first reference point based on a distance from the first reference point to each of first candidate reference points adjacent to the first reference point in the waveform of the biosignal, and determining a pulse sharpness level corresponding to the second reference point based on a distance from the second reference point to each of second candidate reference points adjacent to the second reference point in the waveform of the biosignal.

The determining of the pulse sharpness level corresponding to the first reference point may include determining the pulse sharpness level corresponding to the first reference point based on an angle formed between a first line connecting the first reference point to a first candidate reference point adjacent to the first reference point in the waveform of the biosignal and a second line connecting the first reference point to another first candidate reference point adjacent to the first reference point.

The determining of the pulse direction may include determining the pulse direction based on a pulse direction strength of respective pulse sharpness levels of the first reference points and respective pulse sharpness levels of the second reference points.

The determining of the pulse direction may include determining a current pulse direction strength based on whether a current reference point is the first reference point or the second reference point and on a pulse sharpness level corresponding to the current reference point, and determining a subsequent pulse direction strength based on whether a subsequent reference point is the first reference point or the second reference point, a pulse sharpness level corresponding to the subsequent reference point, and the current pulse direction strength.

The determining of the pulse direction may include determining the waveform of the biosignal to be in a first pulse direction in response to the pulse direction strength being greater than a threshold value, and determining the waveform of the biosignal to be in a second pulse direction in response to the pulse direction strength being less than or equal to the threshold value.

The determining of the feature point of the biosignal may include determining the feature point of the biosignal based on a first feature point determining method in response to the pulse direction of the biosignal being determined to be the first pulse direction, and determining the feature point of the biosignal based on a second feature point determining method in response to the pulse direction of the biosignal being determined to be the second pulse direction.

The determining of the pulse direction may include determining the pulse direction based on a result of comparing a sum of the pulse sharpness levels of the first reference points and a sum of the pulse sharpness levels of the second reference points.

The method may include removing a direct current (DC) component from the biosignal, and wherein the extracting of the reference points may include extracting the reference points from a waveform of the biosignal from which the DC component is removed.

The method may include removing high-frequency noise from the biosignal by filtering the biosignal from which the DC component is removed, and wherein the extracting of the reference points may include extracting the reference points from a waveform of the biosignal from which the high-frequency noise is removed.

The determining of the feature point of the biosignal may include determining the feature point of the biosignal based on the first reference point or the second reference point based on the pulse direction.

The determining of the feature point of the biosignal may include applying a low-pass filter to the waveform of the biosignal, determining a sum of slopes based on a time with respect to a waveform of the biosignal to which the low-pass filter is applied based on the pulse direction, and determining the feature point of the biosignal based on the sum of slopes and a threshold value.

The threshold value may adaptively vary depending on a change in the biosignal.

The candidate reference points may include first candidate reference points corresponding to maximum points and second candidate reference points corresponding to minimum points.

In another general aspect, there is provided a biosignal processing apparatus including at least one processor configured to extract reference points from a waveform of a biosignal, establish a pulse direction of the biosignal based on the extracted reference points, and determine a feature point of the biosignal based on a feature point determining method corresponding to the pulse direction.

In another general aspect, there is provided a biosignal processing apparatus including at least one processor configured to extract reference points from a waveform of a biosignal, establish a pulse sharpness level corresponding to each of the reference points, and determine a feature point of the biosignal based on the pulse sharpness level, wherein the pulse sharpness level indicates a level of a rapid change in the waveform of the biosignal based on a reference point.

Other features and aspects will be apparent from the following detailed description, the drawings, and the claims.

Figure 1:
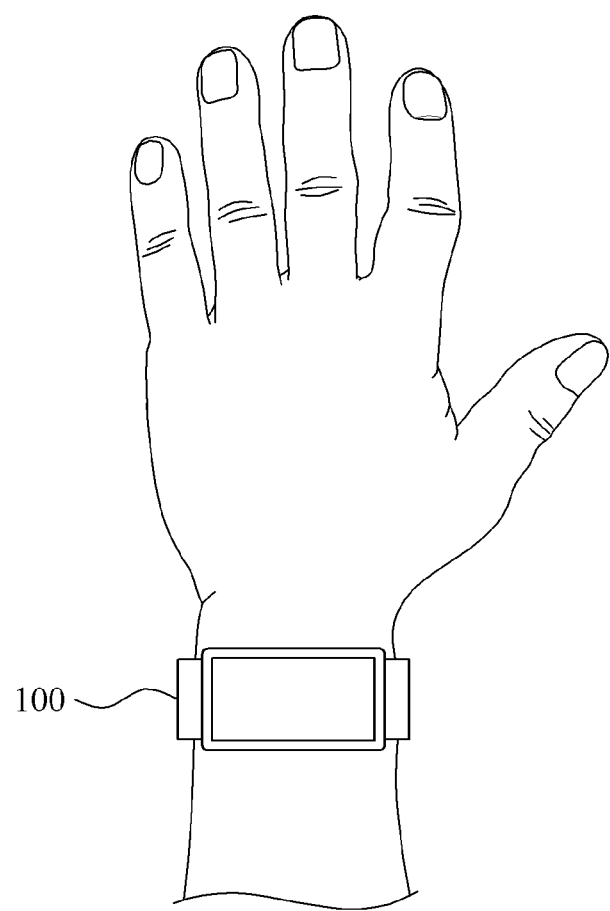
FIG. 1 is a diagram illustrating an example of a wearable device measuring a biosignal.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art after a full understanding of the present disclosure. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The terminology used herein is for the purpose of describing particular examples only and is not intended to be limiting the disclosure. As used herein, the singular forms "a," "an," and "the," are intended to include the plural forms as well, unless the context clearly indicates otherwise.

Terms such as first, second, A, B, (a), (b), and the like may be used herein to describe components. Each of these terminologies is not used to define an essence, order or sequence of a corresponding component but used merely to distinguish the corresponding component from other component(s). For example, a first component may be referred to a second component, and similarly the second component may also be referred to as the first component.

It should be noted that if it is described in the specification that one component is "connected," "coupled," or "joined" to another component, a third component may be "connected," "coupled," and "joined" between the first and second components, although the first component may be directly connected, coupled or joined to the second component. In addition, it should be noted that if it is described in the specification that one component is "directly connected" or "directly joined" to another component, a third component may not be present therebetween.

Examples to be described hereinafter may be applied to extract a signal feature, for example, a feature point, from a biosignal and to determine bioinformation using the extracted signal feature. For convenience of description, the present disclosure provides an example of extracting a signal feature from a photoplethysmogram (PPG) signal, but the examples to be described hereinafter are not limited thereto. Extracting a signal feature from other types of biosignals, such as, for example, an electrocardiogram (ECG) signal, a blood oxygen saturation level ($SpO_2$), a ballistocardiogram (BCG) signal, an electroencephalogram (EEG) signal, or an electromyogram (EMG) signal is also considered to be well within the scope of the present disclosure.

FIG. 1 is a diagram illustrating an example of a wearable device 100 measuring a biosignal.

Referring to FIG. 1, in an example, the wearable device 100 of a band type or a watch type is worn around a wrist of a user to measure and analyze a biosignal from a body of the user. In an example, the wearable device 100 continuously and noninvasively monitors a biosignal of the user. The biosignal includes bioinformation or biometrics, of the body of the user, and is measured in a form, such as, for example, a PPG signal, an ECG signal, an EMG signal. Based on the measured biosignal, various pieces of bioinformation associated with health of the user may be determined.

In an example, the wearable device 100 measures a PPG signal from the wrist of the user through a sensor, extracts various signal features associated with a propagation wave or a reflection wave from the measured PPG signal, and estimates cardiovascular information. The estimated cardiovascular information includes information, such as, for example, a blood pressure and a vascular stiffness, based on the extracted signal features. In an example, the sensor is located on a strap of the wearable device 100 to measure, as the PPG signal, a change in blood flow in a radial artery. The PPG signal may include information on a change in blood flow caused by a heartbeat. The wearable device 100 calculates a heart rate of the user by analyzing a change in the PPG signal, and estimates the cardiovascular information based on the calculated heart rate. The wearable device 100 provides exercise coaching information to the user based on, for example, a heart rate and a blood pressure that are determined based on the PPG signal.

The measurement of a biosignal, such as, for example, a PPG signal, may be affected by respiration and intentional movement of a user, and thus extracting an accurate feature point from the biosignal may be needed to obtain useful information from the biosignal. Further, in a mobile environment it is useful to use less resources and extract a biosignal more rapidly. Examples to be described hereinafter may provide a method to satisfy all the needs described in the foregoing.

Figure 2A:
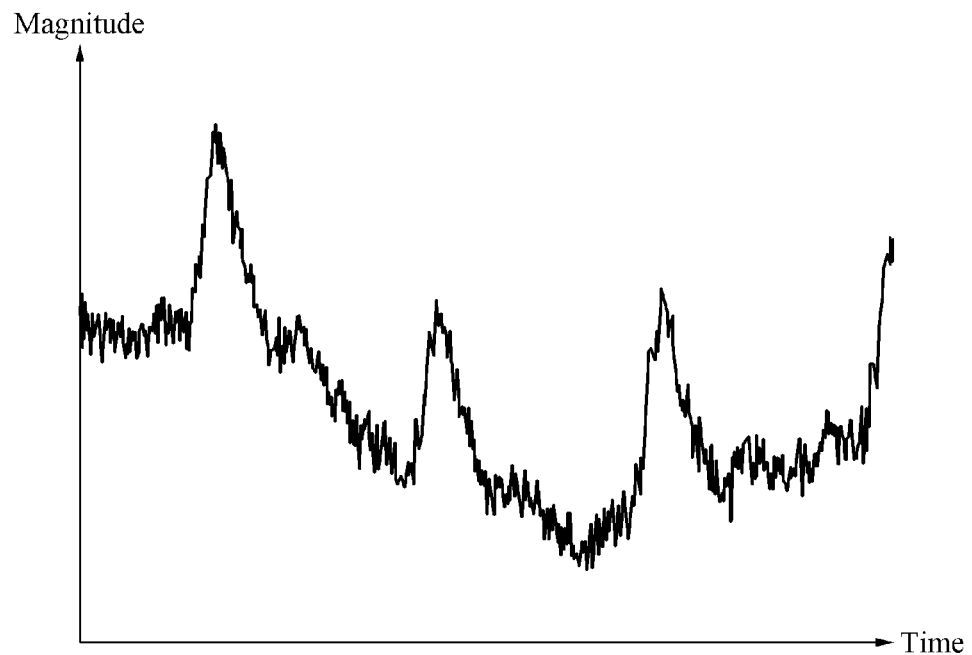
FIGS. 2A and 2B are diagrams illustrating examples of a photoplethysmogram (PPG) signal measured through a sensor.
Figure 2B:
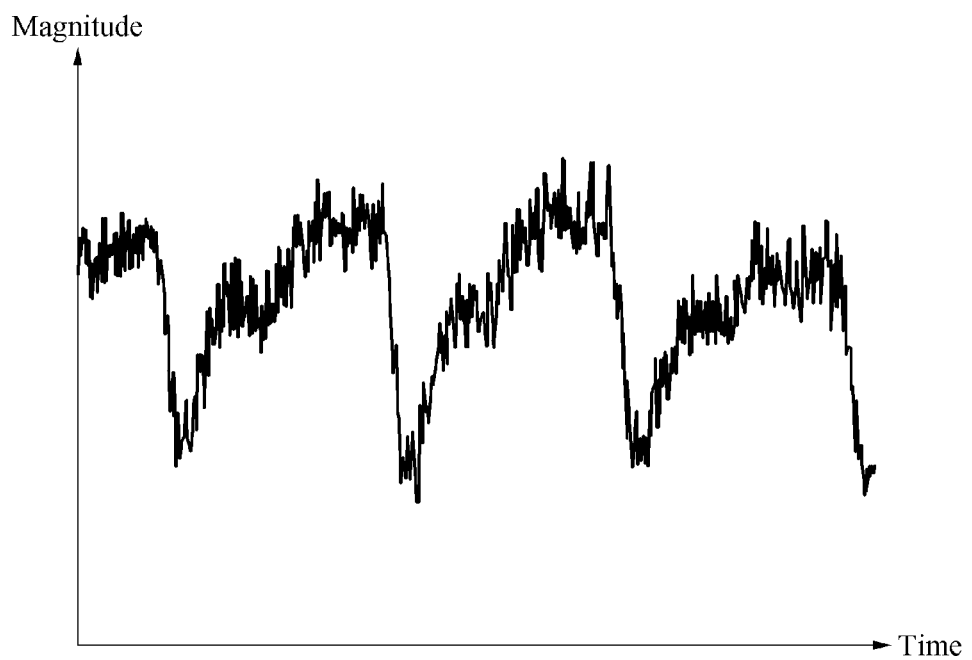

FIGS. 2A and 2B are diagrams illustrating examples of a PPG signal measured through a sensor.

Measurement of a PPG signal is affected by noise, such as, for example, a motion artifact. Thus, a PPG signal measured through a sensor may include a noise component caused by a respiratory activity and a physical movement of a user, in addition to a signal component associated with target bioinformation. When a user wearing the wearable device 100 illustrated in FIG. 1 around a wrist of the user moves the wrist, for example, turns the wrist, inversion of the PPG signal may occur. Such an inversion of the PPG signal may occur when there is a change in the pressure between a skin surface of a radial artery and the sensor configured to sense the PPG signal changes. In another example, the inversion of the PPG signal may occur when a sensing location of the sensor changes on the skin surface.

FIG. 2A is a diagram illustrating a PPG signal waveform measured when a user places a wrist of the user in a neutral position, for example, in a state in which a thumb is placed higher than a little finger. Referring to FIG. 2A, a pulse of a PPG signal faces upwards. FIG. 2B is a diagram illustrating a PPG signal waveform measured when the user turns the wrist from the neutral position. In contrast to the PPG signal waveform illustrated in FIG. 2A, a pulse of a PPG signal faces downwards. As described above, a PPG signal waveform may be reversed based on a posture of a wrist, and thus determining which direction a pulse of a PPG signal faces may be important to extract an accurate signal feature from the PPG signal. In detecting a signal feature from a biosignal, a pulse direction may be considered to extract a more accurate signal feature.

Figure 3:
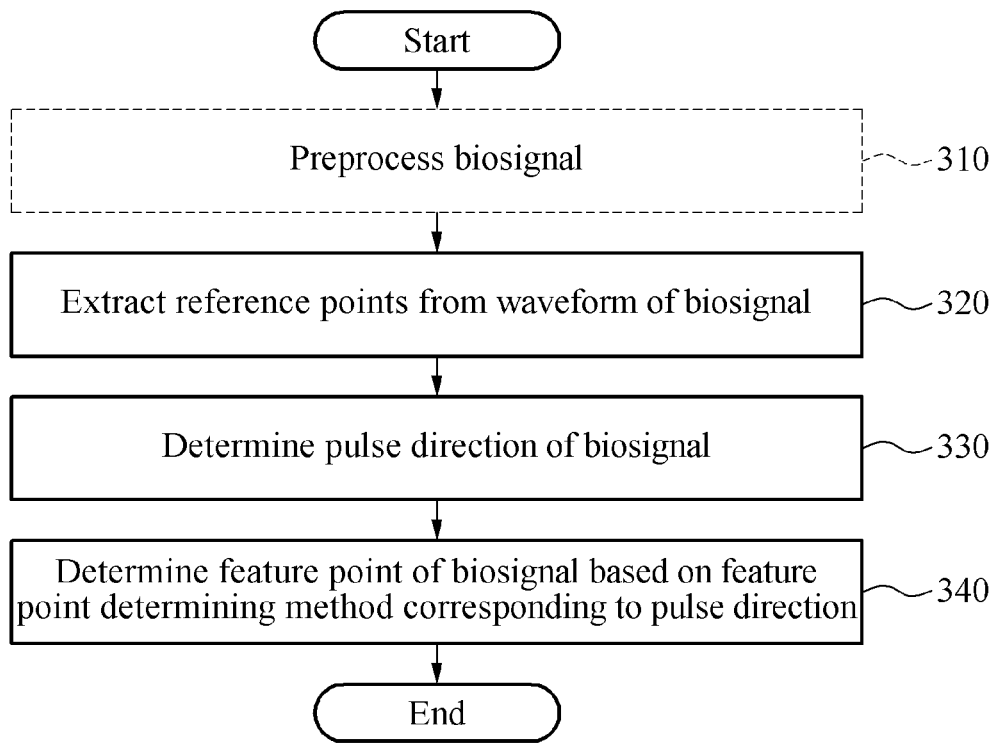
FIGS. 3 and 4 are diagrams illustrating examples of biosignal processing method.
Figure 4:
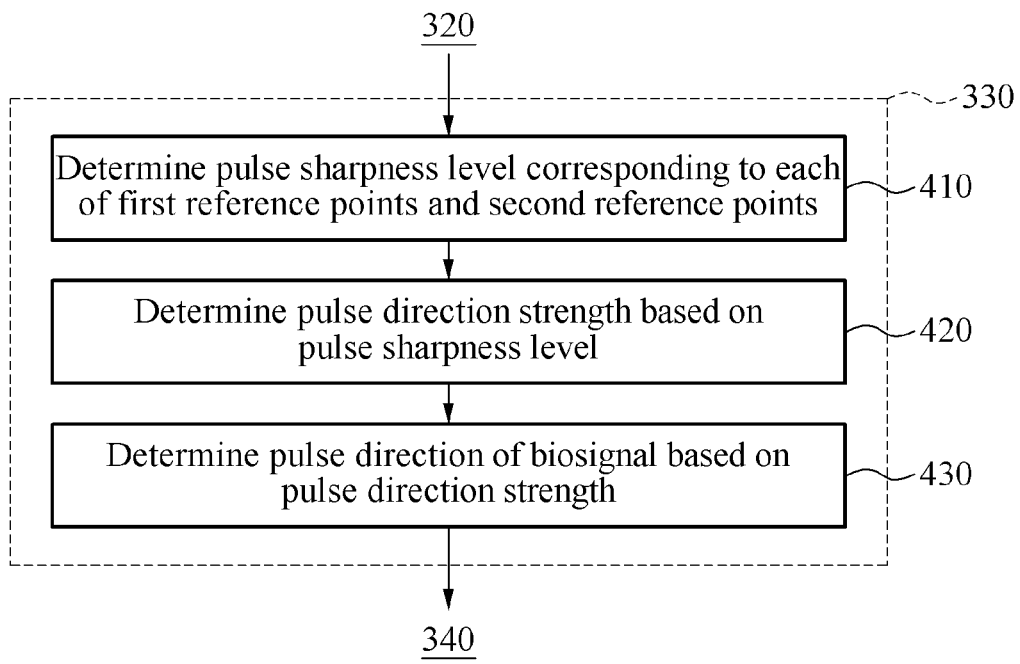

FIGS. 3 and 4 are diagrams illustrating an example of a biosignal processing method. The biosignal processing method may be performed by a biosignal processing apparatus, for example, a biosignal processing apparatus 1400 to be described with reference to FIG. 14. The operations in FIGS. 3 and 4 may be performed in the sequence and manner as shown, although the order of some operations may be changed or some of the operations omitted without departing from the spirit and scope of the illustrative examples described. Many of the operations shown in FIGS. 3 and 4 may be performed in parallel or concurrently. In addition to the description of FIGS. 3 and 4 below, the above descriptions of FIGS. 1-2, are also applicable to FIGS. 3 and 4, and are incorporated herein by reference. Thus, the above description may not be repeated here.

Referring to FIG. 3, in 310, the biosignal processing apparatus selectively preprocesses a biosignal. In an example, the biosignal processing apparatus removes a direct current (DC) component from the biosignal, and removes high-frequency noise from the biosignal by performing filtering on the biosignal from which the DC component is removed.

In 320, the biosignal processing apparatus extracts reference points from a waveform of the biosignal. A reference point indicates a point considered to include bioinformation in the waveform of the biosignal. In an example, the biosignal processing apparatus primarily extracts candidate reference points from the waveform of the biosignal, and determines reference points that satisfy a predetermined or desired standard from among the extracted candidate reference points.

The biosignal processing apparatus extracts first candidate reference points corresponding to a peak, or a maximum point, from the waveform of the biosignal, and extracts second candidate reference points corresponding to a trough, or a minimum point, from the waveform of the biosignal. A peak indicates a point at which a signal value starts decreasing after increasing, and a trough indicates a point at which a signal value starts increasing after decreasing. For example, the biosignal processing apparatus may determine a first candidate reference point based on a highest (or maximum) signal value determined in one time interval of the waveform of the biosignal, and determine a second candidate reference point based on a lowest (or minimum) signal value determined in one time interval of the waveform of the biosignal.

The biosignal processing apparatus may determine a first candidate reference point having a highest signal value among neighboring first candidate reference points to be a first reference point, and determine a second candidate reference point having a lowest signal value among neighboring second candidate reference points to be a second reference point.

In 330, the biosignal processing apparatus determines a pulse direction of the biosignal based on the extracted reference points including the first reference points and the second reference points. For example, the biosignal processing apparatus may determine which direction a pulse of the biosignal faces between a first pulse direction, for example, upwards, and a second pulse direction, for example, downwards. To determine the pulse direction, the biosignal processing apparatus may use a pulse sharpness level corresponding to each of the reference points. The pulse sharpness level indicates how rapidly the pulse of the biosignal changes from a reference point or how sharp a reference point is. The biosignal processing apparatus may determine the pulse sharpness level corresponding to each of the first reference points and the second reference points, and determine the pulse direction based on the determined pulse sharpness levels.

In an example, the biosignal processing apparatus compares a sum of respective pulse sharpness levels of the first reference points to a sum of respective pulse sharpness levels of the second reference points. In an example, the biosignal processing apparatus determines the pulse direction of the biosignal to be the first pulse direction when the sum of the pulse sharpness levels of the first reference points is greater than the sum of the pulse sharpness levels of the second reference points. In another example, the biosignal processing apparatus determines the pulse direction of the biosignal to be the second pulse direction when the sum of the pulse sharpness levels of the first reference points is lesser than or equal to the sum of the pulse sharpness levels of the second reference points.

In another example, as described with reference to FIG. 4, the biosignal processing apparatus may calculate a pulse direction strength based on the pulse sharpness levels of the first reference points and the pulse sharpness levels of the second reference points.

Referring to FIG. 4, in 410, the biosignal processing apparatus determines a pulse sharpness level corresponding to each of the first reference points and the second reference points. The biosignal processing apparatus determines a pulse sharpness level corresponding to a first reference point based on a distance between the first reference point and each of first candidate reference points adjacent to the first reference point. In an example, the pulse sharpness level is determined by an angle formed between a first line connecting the first reference point to a first candidate reference point adjacent to the first reference point and a second line connecting the first reference point to another first candidate reference point adjacent to the first reference point. Similarly, the biosignal processing apparatus determines a pulse sharpness level corresponding to a second reference point based on a distance between the second reference point and each of second candidate reference points adjacent to the second reference point in the waveform of the biosignal.

In another example, the biosignal processing apparatus determines a pulse sharpness level based on a direction between the first reference point and each second candidate reference points adjacent to the first reference point. In an example, the pulse sharpness level is determined by an angle formed between a first line connecting the first reference point to a second candidate reference point adjacent to the first reference point and a second line connecting the first reference point to another second candidate reference point adjacent to the first reference point. Similarly, the biosignal processing apparatus determines a pulse sharpness level corresponding to a second reference point based on a distance between the second reference point and each of first candidate reference points adjacent to the second reference point in the waveform of the biosignal.

In 420, the biosignal processing apparatus determines a pulse direction strength based on the pulse sharpness levels of the first reference points and the pulse sharpness levels of the second reference points. In an example, the biosignal processing apparatus determines a current pulse direction strength based on whether a current reference point is the first reference point or the second reference point and on a pulse sharpness level corresponding to the current reference point. In another example, the biosignal processing apparatus determines a subsequent pulse direction strength based on whether a subsequent reference point is the first reference point or the second reference point, a pulse sharpness level corresponding to the subsequent reference point, and the current pulse direction strength. Through such a process, the biosignal processing apparatus may continuously update a pulse direction strength each time a first reference point and a second reference point appear in the waveform of the biosignal. For example, the pulse direction strength may be calculated based on Equation 4 to be described later.

In 430, the biosignal processing apparatus determines the pulse direction of the biosignal based on the determined pulse direction strength. In an example, the biosignal processing apparatus determines the waveform of the biosignal to be in the first pulse direction in response to the pulse direction strength being greater than a threshold value. In another example, the biosignal processing apparatus determines the waveform of the biosignal to be in the second pulse direction, which is different from the first pulse direction, in response to the pulse direction strength being less than or equal to the threshold value. In an example, a threshold value of the pulse direction strength may be 0.

Referring back to FIG. 3, in 340, the biosignal processing apparatus determines a feature point of the biosignal based on a feature point determining method corresponding to the pulse direction once the pulse direction of the biosignal is determined.

For example, the biosignal processing apparatus determines the feature point of the biosignal based on a first feature point determining method corresponding to the first pulse direction when the pulse direction of the biosignal is determined to be the first pulse direction. In another example, the biosignal processing apparatus determines the feature point of the biosignal based on a second feature point determining method corresponding to the second pulse direction when the pulse direction of the biosignal is determined to be the second pulse direction. The first feature point determining method and the second feature point determining method may be similar in an overall process of determining a feature point, but different in a parameter value to be applied. In another example, the first feature point determining method and the second feature point determining method may be different in the overall process of determining a feature point.

In an example, the biosignal processing apparatus applies a low-pass filter on the waveform of the biosignal, and determines a sum of slopes based on a time with respect to the waveform of the biosignal. In an example, the sum of slopes is calculated based on Equation 5 to be described later. The biosignal processing apparatus compares the sum of slopes to a threshold value, and identifies points in time at which the sum of slopes is greater than the threshold value. In an example, the threshold value may adaptively vary depending on a change in the biosignal. For example, a magnitude of the threshold value may change in proportion to a magnitude of the biosignal. Although a considerable change in the biosignal occurs, the threshold value may adaptively change with the biosignal, and thus, the feature point may be more accurately detected from the waveform of the biosignal. The biosignal processing apparatus may search for a highest signal value or a lowest signal value of the biosignal in an interval around the identified points in time, and determine the retrieved signal values to be the feature point of the biosignal.

In another example, when the pulse direction of the biosignal is determined, the biosignal processing apparatus determines the feature point among previously determined reference points based on the pulse direction. For example, when the pulse direction is determined to be an upward direction, the biosignal processing apparatus determines, to be feature points, first reference points having a pulse sharpness level greater than the threshold value among the previously determined first reference points. In another example, when the pulse direction is determined to be a downward direction, the biosignal processing apparatus determines, to be feature points, second reference points having a pulse sharpness level greater than the threshold value among the previously determined second reference points.

Through the operations described above, a feature point of a biosignal may be rapidly determined at a low computational complexity, and a feature point of a biosignal may be more accurately determined although low-frequency noise is not completely removed. Further, a feature point of a biosignal may be determined robustly against fluctuation and inversion of the biosignal.

FIGS. 5 through 13 illustrate examples of a process of determining a feature point from a PPG signal measured through a sensor.

Figure 5:
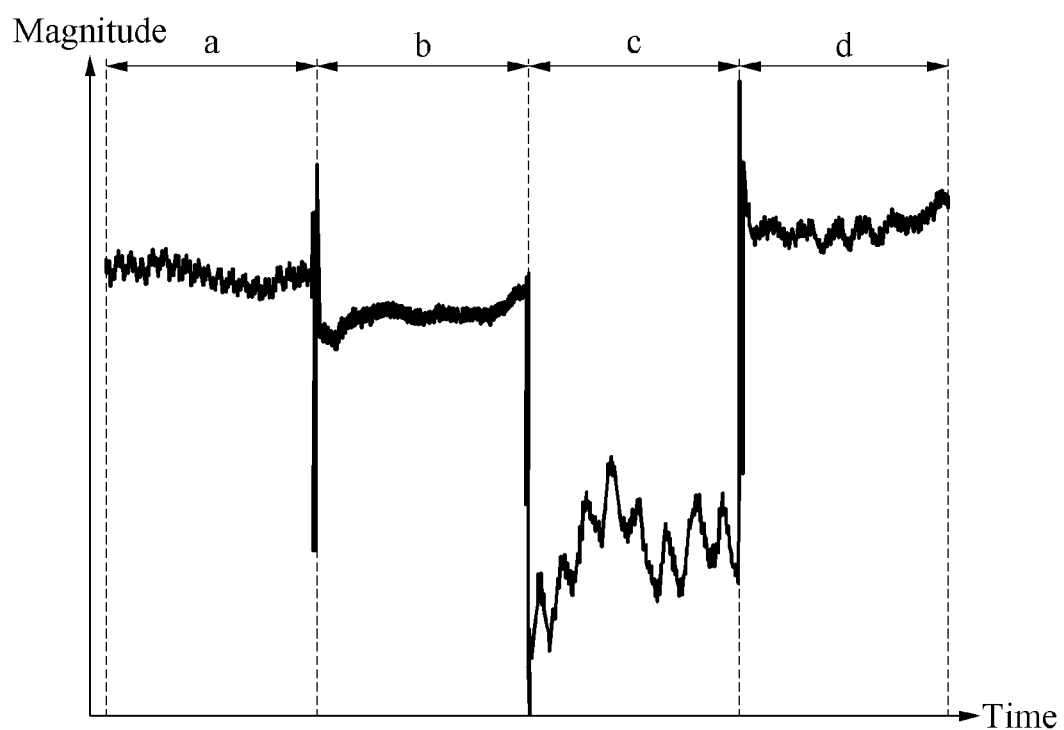
FIG. 5 is a diagram illustrating examples of a waveform of a PPG signal measured in various states.

FIG. 5 is a diagram illustrating examples of a waveform of a PPG signal measured in various states. A variety of waveforms of a PPG signal may appear based on a state of a user. The examples illustrated in FIG. 5 include a waveform "a" of the PPG signal, a waveform "b" of the PPG signal, a waveform "c" of the PPG signal, and a waveform "d" of the PPG signal. The waveform "a" of the PPG signal is measured when the user places a wrist in a neutral position. The waveform "b" of the PPG signal is measured when the user turns the wrist from the neutral position. The waveform "c" of the PPG signal is measured when the user turns the wrist back to the neutral position again from the turned position of the wrist while breathing in more deeply than ordinary. The waveform "d" of the PPG signal is measured when the user turns the wrist from the neutral position again while breading in more deeply than ordinary. The waveforms c and d of the PPG signal may be relatively more rough than the waveforms a and b of the PPG signal.

Figure 6:
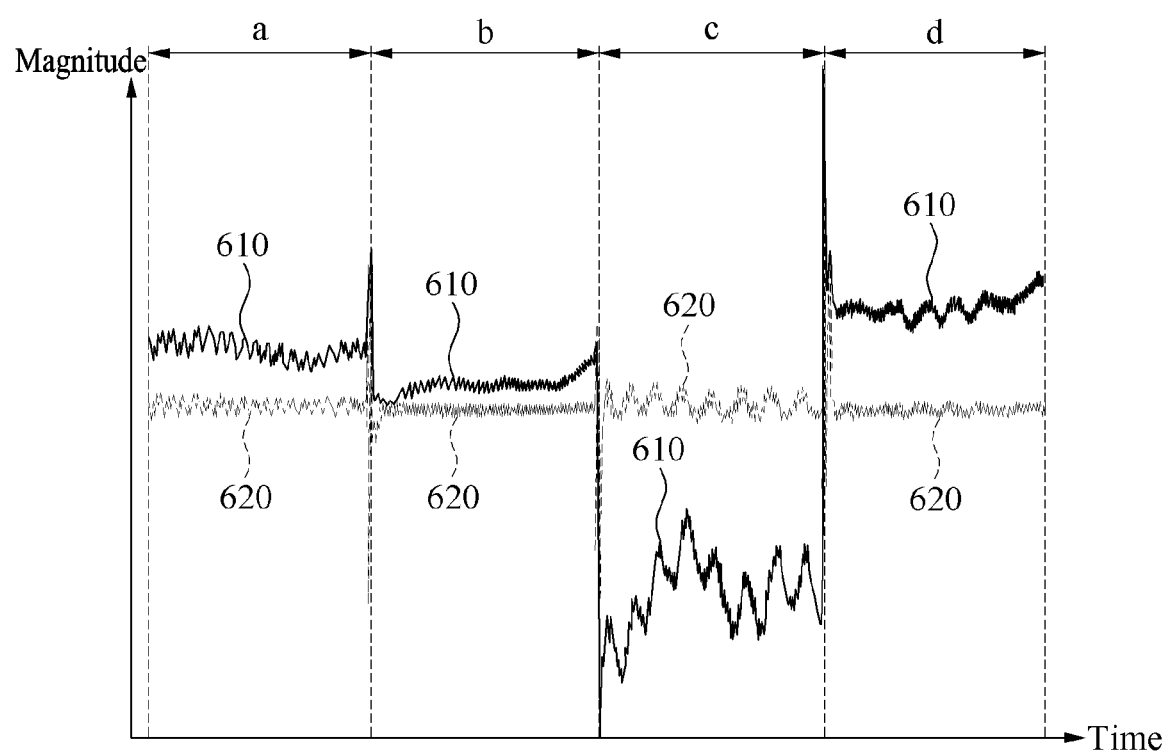
FIG. 6 is a diagram illustrating an example of preprocessing a PPG signal.

FIG. 6 is a diagram illustrating an example of prepro- cessing a PPG signal. When a PPG signal is measured, a biosignal processing apparatus may remove a DC compo- nent from the measured PPG signal. In an example, the biosignal processing apparatus may remove the DC com- ponent from the PPG signal by removing, from a raw PPG signal, an average value of PPG signal values to be con- tinuously sampled through a sensor. Referring to FIG. 6, a waveform 610 indicates a raw PPG signal waveform mea- sured through the sensor in time intervals a, b, c, and d, and a waveform 620 indicates a waveform resulting from removal of a DC component from the raw PPG signal waveform.

After removing the DC component, the biosignal process- ing apparatus may remove high-frequency noise by applying a low-pass filter to the PPG signal from which the DC component is removed. For example, the biosignal process- ing apparatus may apply a hamming window having a 10 hertz (Hz) cutoff frequency to the PPG signal from which the DC component is removed. Through the hamming window, a 10 Hz or higher frequency component may be removed from the PPG signal.

Figure 7:
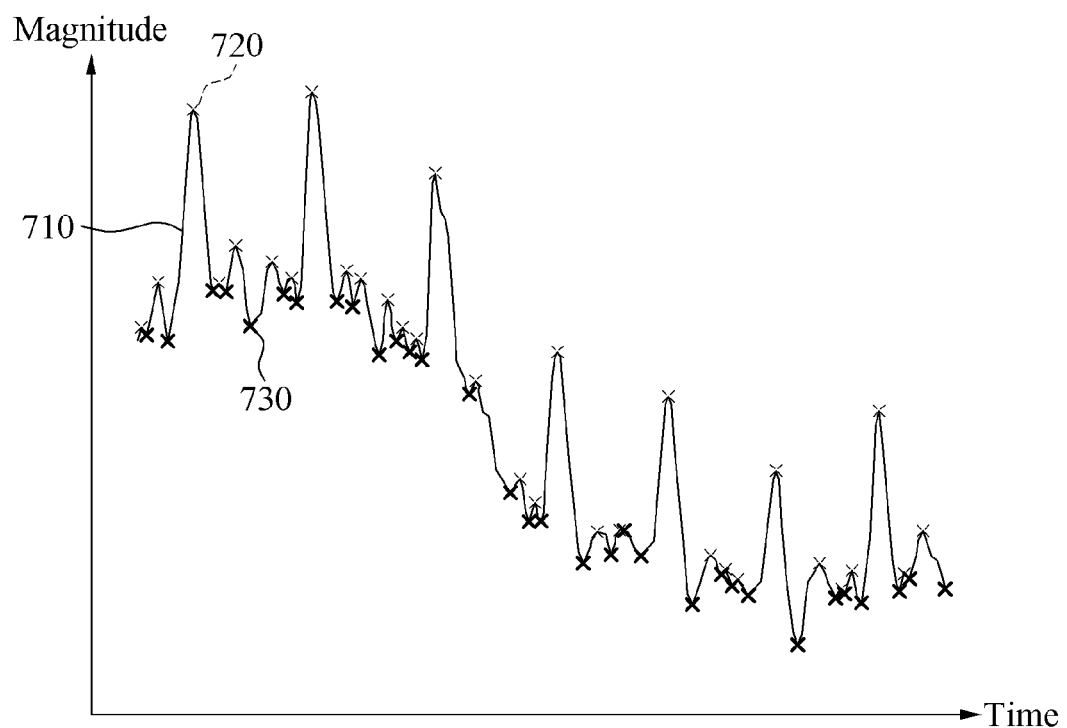
FIG. 7 is a diagram illustrating an example of a process of extracting candidate reference points from a waveform of a PPG signal.

FIG. 7 is a diagram illustrating an example of a process of extracting candidate reference points from a PPG signal waveform.

A biosignal processing apparatus may extract local peaks and troughs as candidate reference points from a measured PPG signal waveform 710. Referring to FIG. 7, the peaks correspond to first candidate reference points 720, and the troughs correspond to second candidate reference points 730. In an example, the biosignal processing apparatus may extract the first candidate reference points 720 and the second candidate reference points 730 from the PPG signal waveform 710 based on Equation 1 below.

$$p(t) = \begin{cases} x(t), & \text{for } x(t) > \{x(t+i) \mid i = -5, -4, \cdots, +4, +5\} \\ x(t), & \text{for } x(t) < \{x(t+i) \mid i = -5, -4, \cdots, +4, +5\} \\ 0, & \text{otherwise} \end{cases} \quad \text{[Equation 1]}$$

In Equation 1, "x(t)" denotes a PPG signal sampled and recorded in a time t, and "i" denotes an integer that does not include 0. If x(t) is a first candidate reference point 720 or a second candidate reference point 730, "p(t)" may have a value of x(t). Otherwise, p(t) may have a value of 0. In Equation 1, among 11 PPG signal values sampled in a time interval based on the time t, a location of a highest signal value may be determined to be the first candidate reference point 720, and a location of a lowest signal value may be determined to be the second candidate reference point 730. However, a scope of values of i may vary without being limited to the scope defined in Equation 1. Here, some of the candidate reference points extracted through such a process may not correspond to a pulse component of the PPG signal. Thus, a process of determining reference points correspond- ing to the target pulse component of the PPG signal may be performed, and a detailed description of the process will be provided with reference to FIG. 8.

Figure 8:
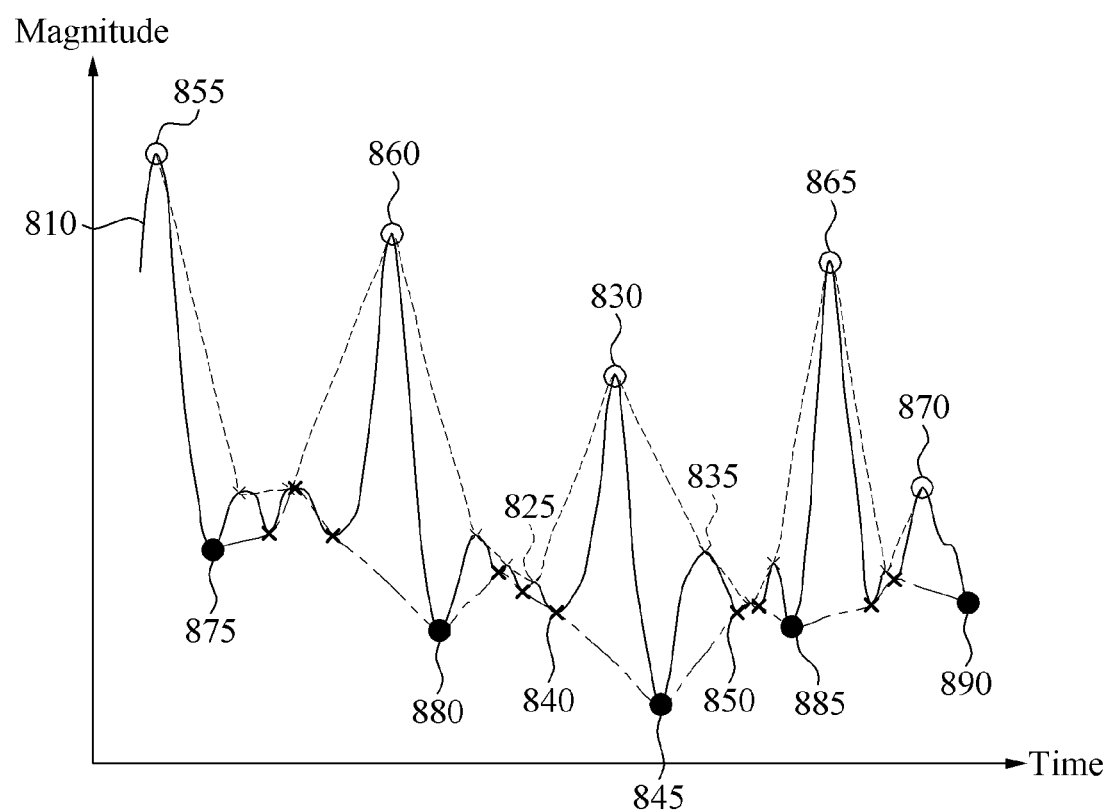
FIG. 8 is a diagram illustrating an example of a process of determining first reference points and second reference points from extracted candidate reference points and determining a pulse sharpness level.

FIG. 8 is a diagram illustrating an example of a process of determining first reference points and second reference points among extracted candidate reference points and deter- mining a pulse sharpness level.

A biosignal processing apparatus may exclude undesir- able candidate reference points and determine reference points to be used to determine a pulse direction by compar- ing each of candidate reference points extracted from a PPG signal waveform 810 to neighboring candidate reference points. Referring to FIG. 8, the biosignal processing appa- ratus may determine, to be a first reference point, a first candidate reference point 830 having a highest signal value among neighboring first candidate reference points 825, 830, and 835. A signal value of a first candidate reference point corresponding to a pulse component of an actual PPG signal may be greater than respective signal values of other neigh- boring first candidate reference points. In addition, the biosignal processing apparatus may determine, to be a second reference point, a second candidate reference point 845 having a lowest signal value among neighboring second candidate reference points 840, 845, and 850. A signal value of a second candidate reference point corresponding to a pulse component of an actual PPG signal may be lower than respective signal values of other neighboring second candidate reference points. FIG. 8 illustrate first reference points 830, 855, 860, 865, and 870 and second reference points 845, 875, 880, 885, and 890 that are determined through the process described in the foregoing.

When the reference points are determined, a pulse sharpness level of each reference point may be determined. Referring to FIG. 8, two lines that connect the first reference point 830 to the first candidate reference points 825 and 835 adjacent to the first reference point 830 are formed, and a pulse sharpness level of the first reference point 830 is calculated based on an angle formed between the two lines. Similarly, two lines that connect the second reference point 845 to the second candidate reference points 840 and 850 adjacent to the second reference point 845 are formed, and a pulse sharpness level of the second reference point 845 is calculated based on an angle formed between the two lines. A detailed description of calculating a pulse sharpness level will be provided with reference to FIG. 9.

Figure 9:
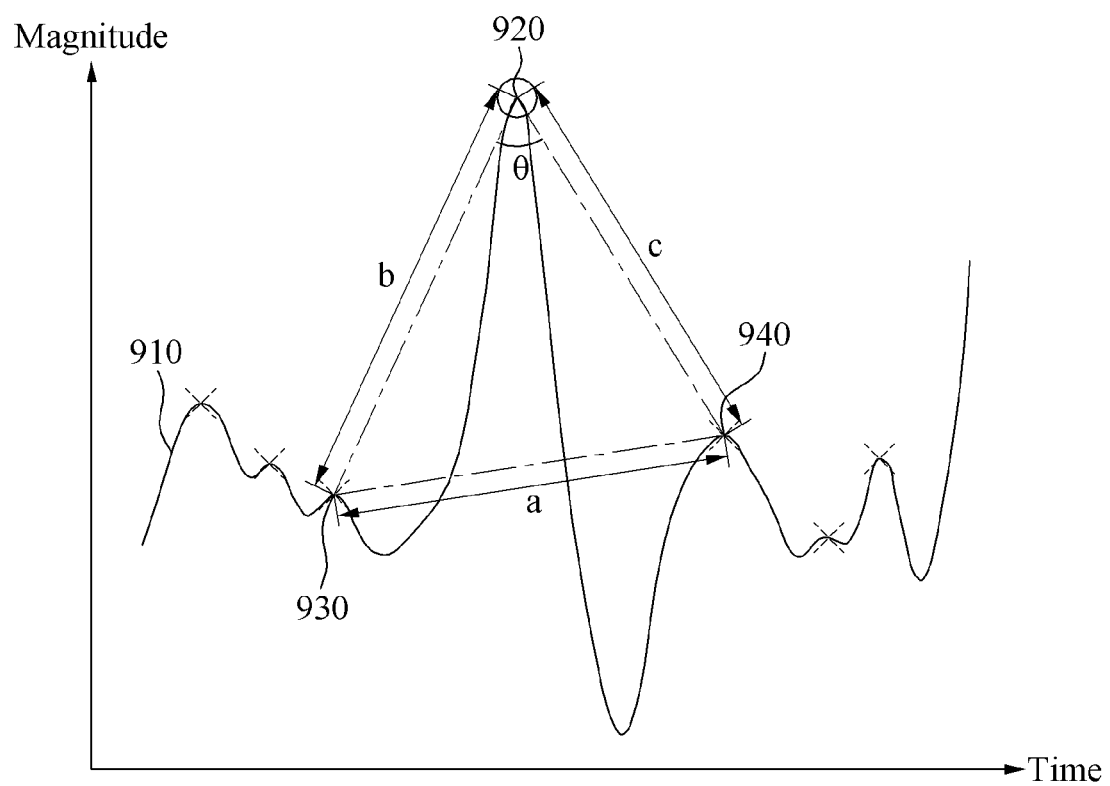
FIG. 9 is a diagram illustrating an example of a process of determining a pulse sharpness level.

FIG. 9 is a diagram illustrating an example of a process of determining a pulse sharpness level.

In an example, a pulse sharpness level of each reference point may be calculated based on a low of cosines. Referring to FIG. 9, a triangle is formed by a line "b" connecting a first reference point 920 determined from a PPG signal waveform 910 to a first candidate reference point 930 adjacent to the first reference point 920, a line "c" connecting the first reference point 920 to another first candidate reference point 940 adjacent to the first reference point 920, and a line "a" connecting the first candidate reference point 930 to the other first candidate reference point 940. A pulse sharpness level of the first reference point 920 may be quantitatively calculated using the triangle.

In an example, the pulse sharpness level of the first reference point 920 may be determined based on an angle θ formed between the lines b and c, and the angle θ may be defined by the second law of cosines represented as Equation 2 below.

$$\cos\theta = \frac{b^2 + c^2 - a^2}{2bc} \quad \text{[Equation 2]}$$

In Equation 2, respective lengths of the lines a, b, and c that forms the triangle may be calculated using a time and a signal value corresponding to each of the points 920, 930, and 940 in the PPG signal waveform 910. An amount of power consumption may be reduced by multiplying the angle θ by 100 to have a range from −100 to +100 and integerizing a value of the angle θ. When the integerized value of the angle θ is close to −100, the angle θ may indicate an obtuse angle. In another example, when the integerized value of the angle θ is close to +100, the angle θ may indicate an acute angle. The pulse sharpness level of the first reference point 920 may be determined based on the integerized value of the angle θ. When the integerized value of the angle θ increases, the pulse sharpness level may increase. The increase in the pulse sharpness level may indicate that a pulse may become sharper. In another example, when the integerized value of the angle θ decreases, the pulse sharpness level may decrease. The decrease in the pulse sharpness level may indicate that the pulse may become smoother.

In another example, the angle θ formed between the lines b and c may be defined by Equation 3 below.

$$\cos^2\theta = \frac{(b^2 + c^2 - a^2)^2}{4 \times b^2 \times c^2} \quad \text{[Equation 3]}$$

To obtain the lengths of the lines a, b, and c, a square root calculation may be needed. However, the angle θ may be approximately estimated based on Equation 3 without the square root calculation of the lengths of the lines a, b, and c. Thus, a computational amount may be reduced. In addition, the pulse sharpness level of the first reference point 920 may be determined based on the obtained value of the angle θ.

Figure 10:
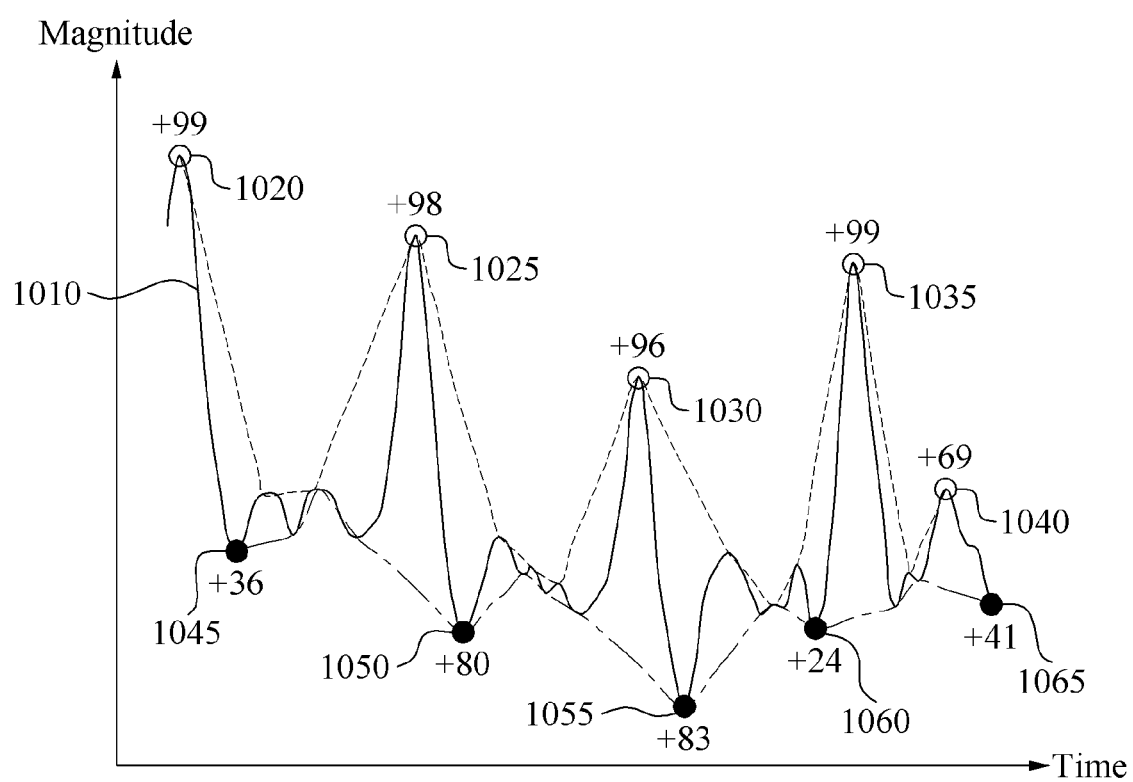
FIG. 10 is a diagram illustrating an example of a pulse sharpness level determined for each of first reference points and second reference points.

A pulse sharpness level of each reference point determined through the above-described process is illustrated in FIG. 10. In the example of FIG. 10, for convenience of description, a pulse sharpness level of each reference point may have a value within a range of −100 through +100 by multiplying the pulse sharpness level by 100. When a pulse sharpness level of a reference point is closer to +100, a pulse component including the reference point may become sharper.

FIG. 10 is a diagram illustrating an example of a PPG signal waveform 1010 in an upward pulse direction. Referring to FIG. 10, when a pulse direction is an upward direction, respective pulse sharpness levels of first reference points 1020, 1025, 1030, 1035, and 1040 may have greater values than respective pulse sharpness levels of second reference points 1045, 1050, 1055, 1060, and 1065. In another example, when the pulse direction is a downward direction, the respective pulse sharpness levels of the second reference points 1045, 1050, 1055, 1060, and 1065 may have greater values than the respective pulse sharpness levels of the first reference points 1020, 1025, 1030, 1035, and 1040.

In an example, a biosignal processing apparatus may determine a pulse direction of the PPG signal waveform 1010 by comparing a first pulse sharpness sum of the pulse sharpness levels of the first reference points 1020, 1025, 1030, 1035, and 1040 to a second pulse sharpness sum of the pulse sharpness levels of the second reference points 1045, 1050, 1055, 1060, and 1065. When the first pulse sharpness sum is greater than the second pulse sharpness sum, the biosignal processing apparatus may determine the pulse direction of the PPG signal waveform 1010 to be the upward direction. In another example, when the second pulse sharpness sum is greater than the first pulse sharpness sum, the biosignal processing apparatus may determine the pulse direction of the PPG signal waveform 1010 to be the downward direction.

In another example, the biosignal processing apparatus may determine a pulse direction strength based on the pulse sharpness levels of the first reference points 1020, 1025, 1030, 1035, and 1040 and the pulse sharpness levels of the second reference points 1045, 1050, 1055, 1060, and 1065, and determine a pulse direction of the PPG signal waveform 1010. The pulse direction strength may indicate which direction between the upward direction and the downward direction a pulse of the PPG signal waveform 1010 is more strongly formed. For example, the biosignal processing apparatus may calculate the pulse direction strength based on Equation 4 below.

$$d_{new} = \frac{(d_{old} \times \beta) + (100 \times \cos\theta \times s)}{(\beta + 1)} \quad \text{[Equation 4]}$$

In Equation 4, "$d_{new}$" and "$d_{old}$" denote a current pulse direction strength and a previous pulse direction strength, respectively. $d_{new}$ may be updated based on a weighted value β each time a reference point is detected. When β is greater, $d_{new}$ may be less affected by $d_{old}$. In Equation 4, a denominator (β+1) may be used for normalization of a value of $d_{new}$. "s" has a value of +1 when a current reference point is a first reference point, and has a value of −1 when the current reference point is a second reference point.

When the value of $d_{new}$ is greater than 0, the biosignal processing apparatus may determine the pulse direction of the PPG signal waveform 1010 to be the upward direction. In another example, when the value of $d_{new}$ is less than 0, the biosignal processing apparatus may determine the pulse direction of the PPG signal waveform 1010 to be the downward direction.

Figure 11:
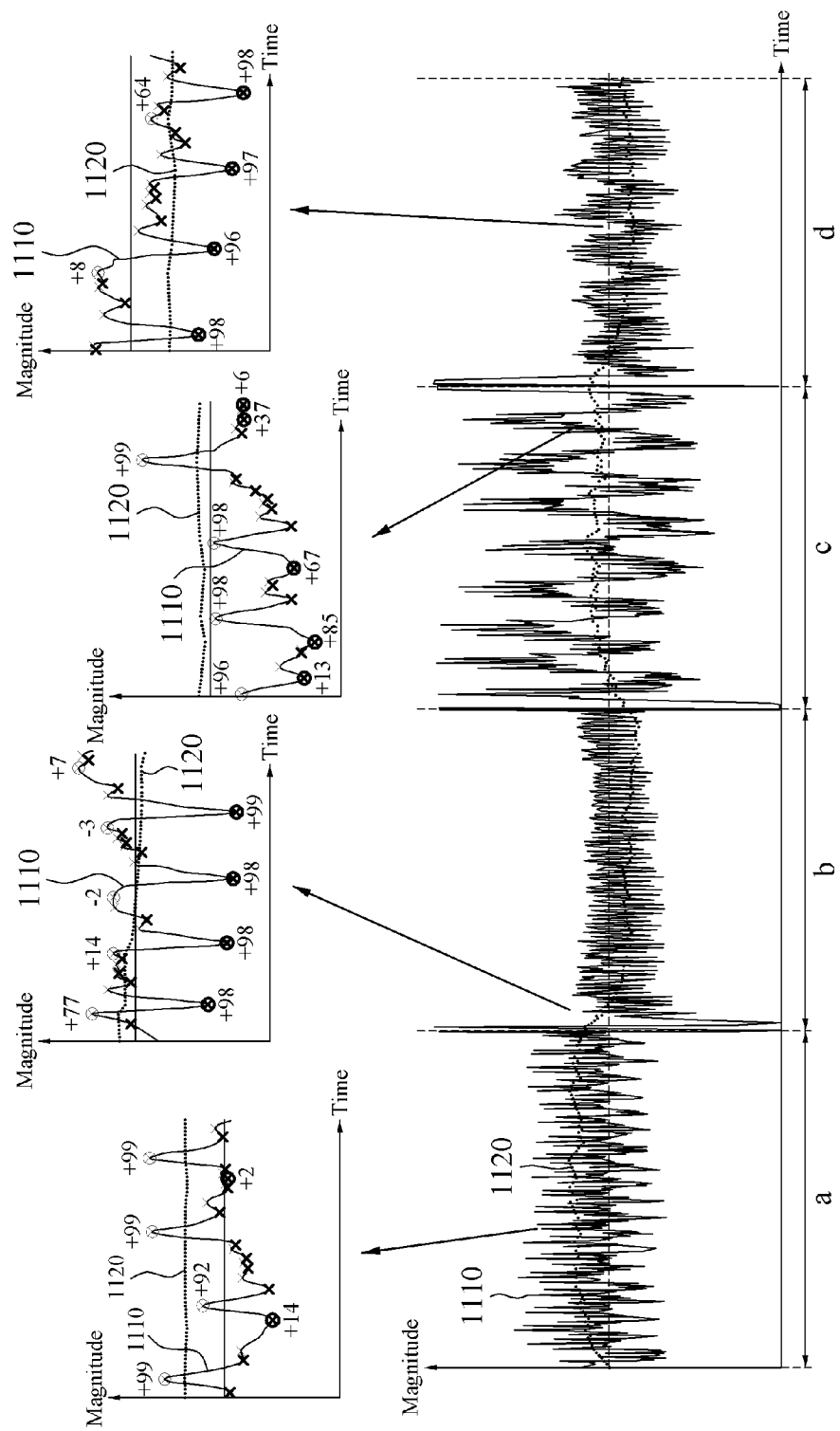
FIG. 11 is a diagram illustrating an example of a pulse direction strength determined for a PPG signal on which preprocessing is performed.

FIG. 11 is a diagram illustrating an example of a pulse direction strength determined for a PPG signal on which preprocessing is performed. Referring to FIG. 11, a pulse of a PPG signal waveform 1110 faces upwards in an interval "a," and a pulse direction strength 1120 may be indicated as a value greater than 0. The pulse of the PPG signal waveform 1110 is reversed to face downwards in an interval "b," and thus the pulse direction strength 1120 in the interval a decreases gradually to become less than 0. In intervals "c" and "d," the PPG signal waveform 1110 may significantly fluctuate due to a deep breath. However, a biosignal processing apparatus may accurately obtain the pulse direction strength 1120 in the intervals c and d irrespective of such a rapid fluctuation of the PPG signal waveform 1110. Thus, the pulse direction of the PPG signal waveform 1110 may be accurately determined.

Figure 12:
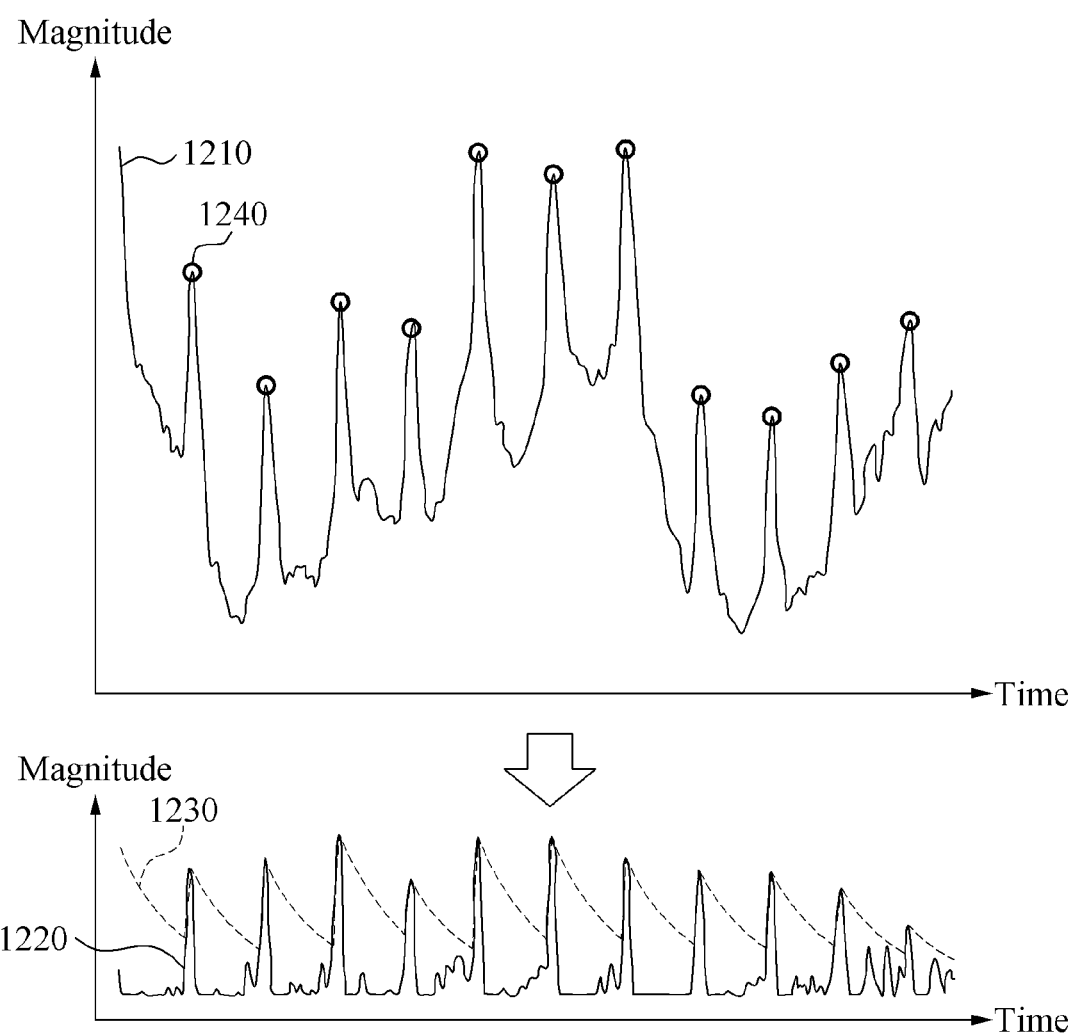
FIGS. 12 and 13 are diagrams illustrating examples of a process of determining a feature point of a PPG signal based on a pulse direction.
Figure 13:
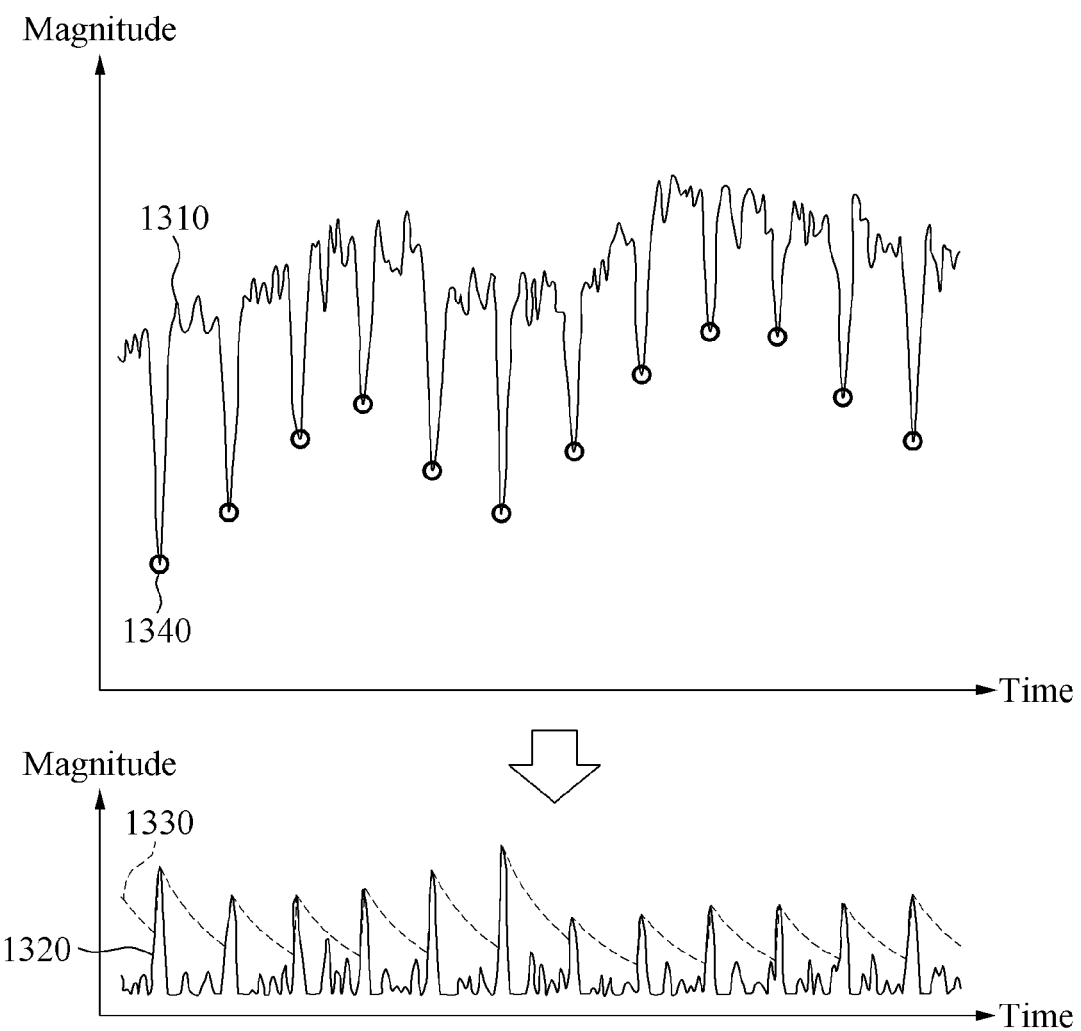

FIGS. 12 and 13 are diagrams illustrating examples of a process of determining a feature point of a PPG signal based on a pulse direction.

After a pulse direction of a PPG signal is determined, a feature point of the PPG signal, for example, a biosignal on which preprocessing is performed as described with FIG. 6, may be determined based on the determined pulse direction. In an example, a biosignal processing apparatus may apply a low-pass filter to a PPG signal waveform, and determine a sum of slopes of the PPG signal waveform based on the pulse direction.

In an example, the biosignal processing apparatus may determine a sum of slopes based on a time, for example, a slope sum function SSF, as represented by Equation 5 below.

$$SSF = \sum_{k=i-w}^{i} \Delta u_k, \quad \Delta u_k = \begin{cases} \Delta y_k & : \Delta y_k > 0 \\ 0 & : \Delta y_k \le 0 \end{cases}, \quad \text{[Equation 5]}$$

In Equation 5, "w" denotes a length of a window to be applied to the PPG signal waveform. "$y_k$" denotes the PPG signal to which the low-pass filter is applied. "$\Delta y_k$" denotes a value of $y_k - y_{k-1}$. Using the sum of slopes, the feature point may be accurately determined from the PPG signal waveform without using an additional high-pass filter.

The biosignal processing apparatus may determine the feature point of the PPG single based on the sum of slopes SSF and a threshold value. In an example, the threshold value may adaptively change based on a change in the PPG signal. For example, the threshold value may change in proportion to a current signal value of the PPG signal. For example, the threshold value may be adaptively determined based on Equation 6 below.

$$AT_k = AT_{k-1} + S_r \frac{(V_{prev} + std_{PPG})}{F_s} \quad \text{[Equation 6]}$$

In Equation 6, "$\Delta T_k$" denotes a threshold value in a time k, "$S_r$" denotes a slope changing rate in the PPG signal waveform. "$V_{prev}$" denotes a previous pulse signal value, and "$std_{PPG}$" denotes a standard deviation of the PPG signal. "Fs" denotes a sampling frequency.

Based on Equation 6, the threshold value may decrease until the PPG signal becomes greater than the threshold value. Thus, although a signal value of the PPG signal fluctuates significantly due to a respiratory activity or a physical movement, the feature point may be accurately detected.

As illustrated in FIG. 12, when a pulse direction of a PPG signal waveform 1210 is determined to be an upward direction, a slope sum 1220 may be calculated based on Equation 5. A threshold value 1230 based on Equation 6 may be adaptively determined depending on a change in the PPG signal waveform 1210, and feature points 1240 may be determined from the PPG signal waveform 1210 based on the threshold value 1230. For example, a location greater than the threshold value 1230 may be identified from the slope sum 1220, and a signal location having a highest signal value in one time interval based on the identified location in the PPG signal waveform 1220 may be determined to be the feature point.

As illustrated in FIG. 13, when a pulse direction of a PPG signal waveform 1310 is determined to be a downward direction, a value of Auk may be replaced by a value of $-\Delta u_k$ in Equation 5, and a positive slope value 1320 may be obtained. Similar to the example of FIG. 12, a threshold value 1330 based on Equation 6 may be adaptively determined depending on a change in the PPG signal waveform 1310, and feature points 1340 may be determined from the PPG signal waveform 1310 based on the threshold value 1330. For example, a location greater than the threshold value 1330 may be identified from the slope sum 1320, and a signal location having a lowest signal value in one time interval based on the identified location in the PPG signal waveform 1310 may be determined to be the feature point.

Through such a process described in the foregoing, feature points may be detected from a PPG signal waveform, more accurately and rapidly, irrespective of a pulse direction of the PPG signal waveform.

Figure 14:
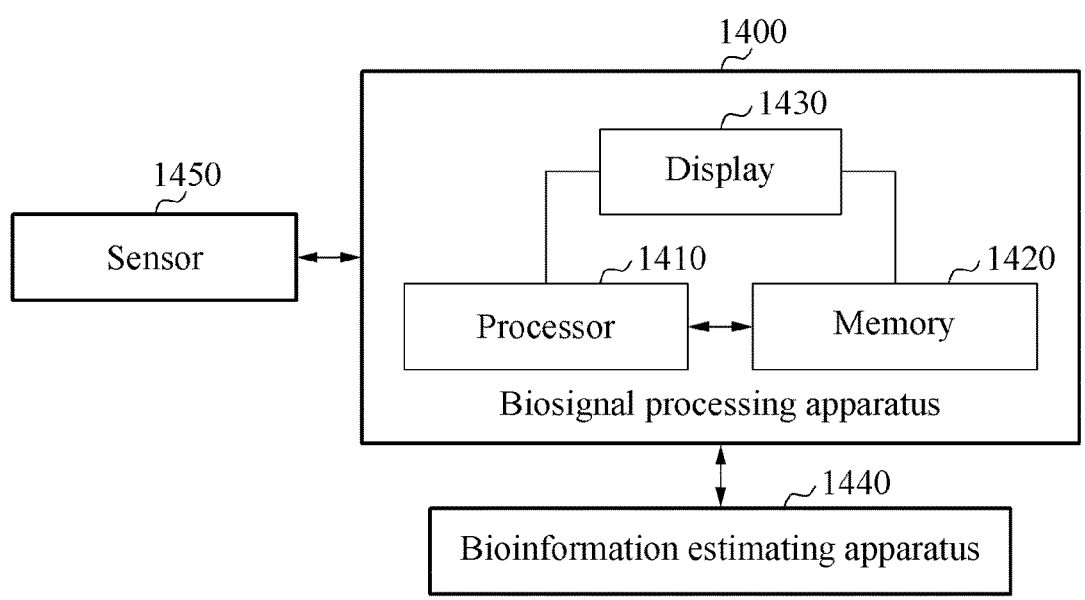
FIG. 14 is a diagram illustrating an example of a biosignal processing apparatus.

FIG. 14 is a diagram illustrating an example of a biosignal processing apparatus 1400.

Referring to FIG. 14, the biosignal processing apparatus 1400 receives, from a sensor 1450, a biosignal sensed by the sensor 1450, and detects feature points from the received biosignal. Information about the detected feature points is transferred to a bioinformation estimating apparatus 1440, and the bioinformation estimating apparatus 1440 estimates bioinformation, such as, for example, a blood pressure and a heart rate, based on the information about the feature points. The bio-information, such as, for example, a blood pressure and a heart rate is displayed on a display 1430.

In an example, the biosignal processing apparatus 1400 may be embedded in the wearable device 100 illustrated in FIG. 1 to operate, and include at least one processor 1410 and memory 1420. The processor 1410 performs at least one operation described with reference to FIGS. 1 through 13. For example, the processor 1410 may extract reference points from a waveform of a biosignal, determine a pulse direction of the biosignal based on the extracted reference points, and determine a feature point of the biosignal based on a feature point determining method corresponding to the determined pulse direction. The processor 1410 may determine a pulse sharpness level corresponding to each of the reference points, and determine the feature point of the biosignal based on the pulse sharpness level. The processor 1410 may be embodied by an array of logic gates, and it is obvious to one of ordinary skill in the art that the processor 1410 may be embodied by hardware in other forms.

The memory 1420 stores instructions to perform at least one operation described with reference to FIGS. 1 through 13, or stores data and results obtained during an operation of the biosignal processing apparatus 1400. In some examples, the memory 1420 may include a non-transitory computer-readable medium, for example, a high-speed random access memory, and/or a nonvolatile computer-readable medium (e.g, at least one disk storage device, flash memory device, and other nonvolatile solid-state memory device).

In an example, the processor 1410 generates bioinformation, such as, for example, a blood pressure and a heart rate that is displayed on a display 1430. The display 1430 may be a physical structure that includes one or more hardware components that provide the ability to render a user interface and/or receive user input. The display 1430 can encompass any combination of display region, gesture capture region, a touch sensitive display, and/or a configurable area. The display 1430 can be embedded in the biosignal processing apparatus 1400 or may be an external peripheral device that may be attached and detached from the biosignal processing apparatus 1400. The display 1430 may be a single-screen or a multi-screen display. A single physical screen can include multiple displays that are managed as separate logical displays permitting different content to be displayed on separate displays although part of the same physical screen. The display 1430 may also be implemented as an eye glass display (EGD), which includes one-eyed glass or two-eyed glasses.

As a non-exhaustive illustration only, the biosignal processing apparatus 1400 may be embedded in or interoperate with various digital devices such as, for example, a mobile phone, a cellular phone, a smart phone, a wearable smart device (such as, for example, a ring, a watch, a pair of glasses, glasses-type device, a bracelet, an ankle bracket, a belt, a necklace, an earring, a headband, a helmet, a device embedded in the cloths), a personal computer (PC), a laptop, a notebook, a subnotebook, a netbook, or an ultra-mobile PC (UMPC), a tablet personal computer (tablet), a phablet, a mobile internet device (MID), a personal digital assistant (PDA), an enterprise digital assistant (EDA), a digital camera, a digital video camera, a portable game console, an MP3 player, a portable/personal multimedia player (PMP), a handheld e-book, an ultra mobile personal computer (UMPC), a portable lab-top PC, a global positioning system (GPS) navigation, a personal navigation device or portable navigation device (PND), a handheld game console, an e-book, and devices such as a high definition television (HDTV), an optical disc player, a DVD player, a Blue-ray player, a setup box, robot cleaners, a home appliance, content players, communication systems, image processing systems, graphics processing systems, other consumer electronics/information technology (CE/IT) device, or any other device capable of wireless communication or network communication consistent with that disclosed herein. The digital devices may be implemented in a smart appliance, an intelligent vehicle, or in a smart home system.

The digital devices may also be implemented as a wearable device, which is worn on a body of a user. In one example, a wearable device may be self-mountable on the body of the user, such as, for example, a watch, a bracelet, or as an eye glass display (EGD), which includes one-eyed glass or two-eyed glasses. In another non-exhaustive example, the wearable device may be mounted on the body of the user through an attaching device, such as, for example, attaching a smart phone or a tablet to the arm of a user using an armband, incorporating the wearable device in a cloth of the user, or hanging the wearable device around the neck of a user using a lanyard.

The apparatuses, units, modules, devices, and other components illustrated in FIGS. 1 and 14 that perform the operations described herein with respect to FIGS. 3 and 4 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 3 and 4. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 3 through 4 that perform the operations described herein are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A biosignal processing apparatus comprising:
   at least one processor configured to:
   extract reference points from a waveform of a biosignal, the reference points comprising a first reference point having a highest signal value from among neighboring first candidate reference points and a second reference point having a lowest signal value from among neighboring second candidate reference points;
   determine pulse sharpness levels corresponding to each of the first reference point and the second reference point;
   determine feature points of the biosignal based on the pulse sharpness levels; and
   transfer, to a bioinformation estimating apparatus, the feature points such that bioinformation of a user is estimated based on the feature points,
   wherein one or more of the pulse sharpness levels corresponds to an angle formed between a first line connecting the first reference point to a first candidate reference point from among the neighboring first candidate reference points and a second line connecting the first reference point to another first candidate reference point from among the neighboring first candidate reference points.

2. The apparatus of claim 1, wherein the at least one processor is further configured to:
   determine a pulse direction of the biosignal based on the pulse sharpness levels; and
   determine the feature points of the biosignal based on a feature point determining method corresponding to the pulse direction.

3. The apparatus of claim 2, wherein the at least one processor is further configured to:
   determine the pulse sharpness level corresponding to the second reference point based on a distance from the second reference point to each of second candidate reference points adjacent to the second reference point in the waveform of the biosignal.

4. The apparatus of claim 2, wherein the at least one processor is further configured to:
   determine the pulse direction of the biosignal based on a pulse direction strength of respective pulse sharpness levels of the first reference point and respective pulse sharpness levels of the second reference point.

5. The apparatus of claim 4, wherein the at least one processor is further configured to:
   determine a current pulse direction strength based on whether a current reference point is the first reference point or the second reference point and on a pulse sharpness level corresponding to the current reference point; and
   determine a subsequent pulse direction strength based on whether a subsequent reference point is the first reference point or the second reference point, a pulse sharpness level corresponding to the subsequent reference point, and the current pulse direction strength.

6. The apparatus of claim 4, wherein the at least one processor is further configured to:
   determine the waveform of the biosignal to be in a first pulse direction in response to the pulse direction strength being greater than a threshold value, and determining the waveform of the biosignal to be in a second pulse direction in response to the pulse direction strength being less than or equal to the threshold value.

7. The apparatus of claim 6, wherein the at least one processor is further configured to:
   determine the feature points of the biosignal based on a first feature point determining method in response to the pulse direction of the biosignal being determined to be the first pulse direction; and
   determine the feature points of the biosignal based on a second feature point determining method in response to the pulse direction of the biosignal being determined to be the second pulse direction.

8. The apparatus of claim 2, wherein the at least one processor is further configured to:

determine the pulse direction of the biosignal based on a result of comparing a sum of the pulse sharpness levels of the first reference point and a sum of the pulse sharpness levels of the second reference point.

9. The apparatus of claim 2, wherein the at least one processor is further configured to:
determine the feature points of the biosignal based on the first reference point or the second reference point based on the pulse direction.

10. The apparatus of claim 1, wherein the at least one processor is further configured to:
extract candidate reference points corresponding to at least one of a maximum point or a minimum point from the waveform of the biosignal; and
determine the reference points from among the candidate reference points based on signal values of the candidate reference points.

11. The apparatus of claim 10, wherein the at least one processor is further configured to:
determine the candidate reference points based on a highest signal value or a lowest signal value in a time interval of the waveform of the bio signal.

12. The apparatus of claim 1, wherein the at least one processor is further configured to:
apply a low-pass filter to the waveform of the biosignal;
determine a sum of slopes based on a time with respect to a waveform of the biosignal to which the low-pass filter is applied based on a pulse direction of the biosignal; and
determine the feature points of the biosignal based on the sum of slopes and a threshold value.

13. The apparatus of claim 12, wherein the threshold value adaptively varies depending on a change in the biosignal.

14. The apparatus of claim 1, wherein the neighboring first candidate reference points comprise first candidate reference points corresponding to maximum points and the neighboring second candidate reference points comprise second candidate reference points corresponding to minimum points.

15. A biosignal processing apparatus comprising:
at least one processor configured to:
remove a direct current (DC) component from a biosignal;
extract reference points from a waveform of the biosignal from which the DC component is removed, the reference points comprising a first reference point having a highest signal value from among neighboring first candidate reference points and a second reference point having a lowest signal value from among neighboring second candidate reference points;
determine pulse sharpness levels corresponding to each of the first reference points and the second reference point;
determine feature points of the biosignal based on the pulse sharpness levels; and
transfer, to a bioinformation estimating apparatus, the feature points such that bioinformation of a user is estimated based on the feature points,
wherein one or more of the pulse sharpness levels corresponds to an angle formed between a first line connecting a first reference point to a neighboring reference point and a second line connecting the first reference point to another neighboring reference point.

16. The apparatus of claim 15, wherein the at least one processor is further configured to:
remove high-frequency noise from the biosignal by filtering the biosignal from which the DC component is removed, and
extract the reference points from a waveform of the biosignal from which the high-frequency noise is removed.

* * * * *